United States Patent
Urpolahti (10) Patent No.: US 11,492,815 B2
(45) Date of Patent: Nov. 8, 2022

(54) SOUND-PROOF AND HYGIENIC SPACE

(71) Applicant: Vetrospace Oy, Littoinen (FI)

(72) Inventor: Jouko Urpolahti, Littoinen (FI)

(73) Assignee: Vetrospace Oy, Littoinen (FI)

( * ) Notice: Subject to any disclaimer, the term of this patent is extended or adjusted under 35 U.S.C. 154(b) by 4 days.

(21) Appl. No.: 17/057,172

(22) PCT Filed: Apr. 29, 2019

(86) PCT No.: PCT/FI2019/050340
§ 371 (c)(1),
(2) Date: Nov. 20, 2020

(87) PCT Pub. No.: WO2019/224422
PCT Pub. Date: Nov. 28, 2019

(65) Prior Publication Data
US 2021/0230892 A1    Jul. 29, 2021

(30) Foreign Application Priority Data

May 21, 2018  (FI) ..................... 20185467
Jul. 6, 2018   (FI) ..................... 20185625

(51) Int. Cl.
*E04H 1/14*      (2006.01)
*E05D 15/06*     (2006.01)
*E06B 3/46*      (2006.01)

(52) U.S. Cl.
CPC ........... *E04H 1/14* (2013.01); *E05D 15/0652* (2013.01); *E05Y 2201/684* (2013.01);
(Continued)

(58) Field of Classification Search
CPC . A61L 9/18; B01D 46/00; E04B 1/343; E04B 1/62; E04B 1/8218; E04B 5/43;
(Continued)

(56) References Cited

U.S. PATENT DOCUMENTS 1,568,270 A * 1/1926 Cross .................. E05D 15/0643
                                                    16/105
2,950,756 A * 8/1960 Moloney ............... E06B 3/9647
                                                    160/91
(Continued)

FOREIGN PATENT DOCUMENTS

CN    105178631 A    12/2015
CN    206468047 U    9/2017
(Continued)

OTHER PUBLICATIONS

China Patent Office, Office Action, Application No. 201980005577.2, dated Dec. 17, 2020, 8 pages.
(Continued)

*Primary Examiner* — James M Ference
(74) *Attorney, Agent, or Firm* — Ziegler IP Law Group, LLC (57) ABSTRACT

An enclosed space is provided that includes a ceiling, base structure, a plurality of walls, at least one sliding door, a controller, an input air fan and an air outlet. The height and inclination of the base structure are adjustable. The base structure has a first profile; a second profile; and one or more bolts for arranging a tilting angle between the first profile and the second profile. At least one of the walls include an opening for accessing the enclosed space. The door includes two parallel glass panels. The input air fan includes an air filter and the air outlet includes a flow meter configured to provide flow information to the controller.

17 Claims, 8 Drawing Sheets

(52) U.S. Cl.
CPC ..... *E05Y 2800/12* (2013.01); *E05Y 2900/132* (2013.01); *E06B 3/46* (2013.01)

(58) Field of Classification Search
CPC .. E04H 1/125; E04H 1/14; E04H 3/08; E04H 1/12; E05D 15/0652; E05D 15/0656; E05Y 2201/684; E05Y 2600/314; E05Y 2800/12; E05Y 2800/16; E05Y 2900/132; E06B 3/46; F24F 7/02
See application file for complete search history.

(56) References Cited

U.S. PATENT DOCUMENTS

| | | | | |
|---|---|---|---|---|
| 3,464,670 A * | 9/1969 | Rasmussen | | E04H 1/14 |
| | | | | 254/92 |
| 3,566,559 A * | 3/1971 | Dickson | | E04B 2/78 |
| | | | | 52/126.4 |
| 4,037,380 A * | 7/1977 | Pollock | | E04B 2/7818 |
| | | | | 52/475.1 |
| 4,449,337 A * | 5/1984 | Gzym | | E04B 2/825 |
| | | | | 52/126.4 |
| 4,625,476 A * | 12/1986 | Shimada | | E04B 2/7409 |
| | | | | 52/126.4 |
| 5,010,702 A * | 4/1991 | Daw | | E04B 2/7409 |
| | | | | 52/241 |
| 5,038,534 A * | 8/1991 | Pollock | | E04B 2/7451 |
| | | | | 52/126.4 |
| 5,511,348 A * | 4/1996 | Cornell | | E04B 2/827 |
| | | | | 160/351 |
| 5,516,069 A * | 5/1996 | Hanna | | E02D 27/02 |
| | | | | 248/354.1 |
| 6,058,655 A * | 5/2000 | Gravel | | B60P 7/14 |
| | | | | 49/306 |
| 8,097,861 B2 * | 1/2012 | Leben | | B66B 11/0226 |
| | | | | 250/455.11 |
| 9,370,600 B1 * | 6/2016 | DuPuis | | A61L 9/20 |
| 9,617,743 B2 * | 4/2017 | Brown | | E04B 2/56 |
| 9,956,306 B2 * | 5/2018 | Brais | | A61L 2/10 |
| 2002/0100219 A1 * | 8/2002 | Rissone | | E06B 7/2316 |
| | | | | 49/470 |
| 2003/0172592 A1 * | 9/2003 | Krimmel | | G09F 9/33 |
| | | | | 49/409 |
| 2005/0152146 A1 * | 7/2005 | Owen | | A61L 9/20 |
| | | | | 362/294 |
| 2009/0038228 A1 * | 2/2009 | Lee | | E06B 7/23 |
| | | | | 49/360 |
| 2010/0031587 A1 * | 2/2010 | Weeks | | E04F 15/02183 |
| | | | | 52/126.6 |
| 2010/0032589 A1 * | 2/2010 | Leben | | B66B 11/0226 |
| | | | | 250/504 R |
| 2012/0061033 A1 * | 3/2012 | Ona Gonzalez | | E05D 15/58 |
| | | | | 160/205 |
| 2012/0227329 A1 * | 9/2012 | Vosburg | | E05D 15/08 |
| | | | | 49/449 |
| 2014/0052463 A1 * | 2/2014 | Cashman | | G06Q 10/1095 |
| | | | | 705/2 |
| 2014/0326419 A1 * | 11/2014 | Ona-Gonzalez | | E06B 3/5054 |
| | | | | 160/115 |
| 2014/0330579 A1 * | 11/2014 | Cashman | | E04H 1/1222 |
| | | | | 705/2 |
| 2015/0027067 A1 * | 1/2015 | Finney | | E04B 1/34363 |
| | | | | 52/79.5 |
| 2015/0101275 A1 * | 4/2015 | Lefkus, III | | G21F 7/00 |
| | | | | 52/292 |
| 2016/0271281 A1 * | 9/2016 | Clynne | | A61L 2/10 |
| 2018/0193501 A1 * | 7/2018 | Ufkes | | A61L 2/10 |
| 2021/0230892 A1 * | 7/2021 | Urpolahti | | E04H 1/14 |

FOREIGN PATENT DOCUMENTS

| | | |
|---|---|---|
| CN | 107274320 A | 10/2017 |
| KR | 20110005440 A | 1/2011 |
| KR | 20150103483 A | 9/2015 |
| KR | 20150112711 A | 10/2015 |
| KR | 101669226 B1 | 10/2016 |
| KR | 20180001014 U | 4/2018 |
| RU | 2007984 C1 | 2/1994 |
| RU | 124287 U1 | 1/2013 |
| RU | 140580 U1 | 5/2014 |
| WO | 2009133219 A1 | 11/2009 |

OTHER PUBLICATIONS

Finnish Patent and Registration Office, Search Report, U.S. Appl. No. 20/185,625, dated Feb. 4, 2019, 2 pages.
International Search Report and Written Opinion, Application No. PCT/FI2019/050340, dated Sep. 3, 2019, 13 pages.
Russian Patent Office, Search Report, Application No. PCT/FI2019/050340, dated Dec. 27, 2021, 2 pages.

* cited by examiner

SOUND-PROOF AND HYGIENIC SPACE

FIELD

The embodiments herein generally relate to a sound-proof room, and more particularly to a room that is hygienic and sound-proof.

BACKGROUND

A clean space is one of the basic needs in today's lifestyle. Many facilities need a dedicated space for one or more reasons including, without limiting, a telephone booth at an airport or in an office. A user making a call further needs the space to be sound-proof to keep the conversation confidential. As the room may be compact, it needs proper ventilation as well. Thus, there is a need for the space to be sound-proof, hygienic and well ventilated.

Currently available prior art provides a telephone booth that only have a fan inside, but no solution is available to make the space germ-free, sound-proof, and with good air circulation all at the same time.

Document CN 107274320 relates to the field of basic community medical institution combined construction, and proposes a package solution for basic community medical institution combined construction. The package solution for community medical institution construction with the design of the medical building module equipped with basic equipment and the design of the information management system of a supporting community medical institution is provided. The medical building module designed through the design method can be built in a factory from the aspect of the hardware environment of the medical institution, is installed and combined in the field, has the advantages of high degree of standardization and high cost-effective performance, and is widely used in the fields of basic community medical service, pension, field medical service and national defense construction. Document US 2014/330,579 presents a medical kiosk designed to provide tele-medicine services, check-in services, and/or prescription services for a user. The medical kiosk can include a user video conferencing system that is designed to enable the user to have a real-time or near real-time tele-conference with a medical provider located remotely from the medical kiosk.

Accordingly, there remains a need to provide a sound-proof space for the user to keep the calls confidential wherein at the same time the user may feel fresh due to germ-free and well-ventilated environment inside the space.

SUMMARY

A typical enclosed space according to the present description comprises
  a ceiling;
  a base structure, wherein height and inclination of said base structure are arranged to be adjustable wherein said base structure comprises
    a first profile;
    a second profile; and
    one or more bolts for arranging a tilting angle between said first profile and said second profile;
  a plurality of walls, wherein at least one of the walls comprises an opening to allow access to said enclosed space;
  at least one sliding door arranged to close the opening, wherein said sliding door comprises two parallel glass panels;
  a controller;
  an input air fan equipped with an air filter; and
  an air outlet equipped with a flow meter configured to provide flow information to said controller;
  wherein said controller is configured to control said input air fan based on the flow information from said flow meter.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications

BRIEF DESCRIPTION OF THE DRAWINGS

The embodiments herein will be better understood from the following detailed description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The enclosed space includes: a ceiling; a base structure; a plurality of walls, wherein at least one of the walls comprises an opening to allow access to said enclosed space; at least one sliding door arranged to close the opening, wherein said sliding door comprises two parallel glass panels; a controller, an input air fan equipped with an air filter, and an air outlet equipped with a flow meter configured to provide flow information to said controller. The controller is configured to control the input air fan based on the flow information from the flow meter. The height and inclination of the base structure are arranged to be adjustable. The input air fan and the output air pipe are preferably mounted on the ceiling.

The adjustable height and inclination of the enclosed space makes the installation of the enclosed space easy also at uneven surfaces.

According to an embodiment, the enclosed space further comprises a sensor configured to provide presence information to said controller, and said controller is configured to control said light source based on the presence information from said sensor. According to another embodiment, the enclosed space comprises a light source configured to emit light alternately in the visible range and in a dedicated cleaning range.

The light source thus provides illumination into the space. The light source is also configured to emit light in a dedicated cleaning range. Such dedicated cleaning range light is used to kill the germs inside the enclosed space. In an embodiment, the light source emits ultraviolet or blue light to kill the germs inside the enclosed space and to make the space hygienic. The light source may be installed in any of the walls of the space, or on the ceiling. The enclosed space may also comprise more than one light sources, which may emit light at similar or different wavelengths. In an embodiment the light source may be configured to emit light alternately in the visible range and in the dedicated cleaning range.

The flow meter can be used to monitor that the enclosed space is substantially air tight. Indeed, if the amount of air flowing out does not correlated with the amount of air flowing in there might be a problem with the enclosed space (such as door partially being open or a problem with seals etc. of the space).

In an embodiment, the opening to allow access to the enclosed space may include a door with a handle. In another embodiment, the door may be a sliding door configured to run between an upper track and a lower track with the help of one or more rollers. In another embodiment, the lower track may include an H-profile that may further include a plurality of springs. According to another embodiment, the sliding door optionally includes two glass panels arranged to slide in opposite sides of a wall of the enclosed space, most typically of the wall comprising the opening to allow access to the space. In yet another embodiment, the sliding door comprises a low friction part arranged on a surface part of the sliding door.

The plurality of springs produce a force which moves low friction part downwards. The plurality of springs are selected from the springs with spring constants having sufficient force to keep the door up, but to allow the door also to be horizontal with respect to the ground. The plurality of springs keep the low friction part in contact with the lower track when the door is slid.

According to another aspect of the present disclosure, the sliding door further comprises a stopper to stop the sliding door, a protrusion, a rubber part to support the protrusion, and a plurality of brushes arranged to prevent air flow. The protrusion forms part of a seal arrangement to prevent air leakage from the enclosed space.

The protrusion prevents air leakage from the enclosed space and maintains the pressure inside the space. The protrusion is a part of the seal arrangement to limit the amount of air flowing out from the space when the door is closed. In an embodiment, the low friction part may run in the protrusion of the lower track. The base structure comprises a first profile, a second profile, and one or more bolts for arranging a tilting angle between the first profile and the second profile. In an embodiment, the second profile is arrangeable to be in contact with the ground and is an integral part of the floor of the enclosed space. Tilting of the wall element is achieved when the user turns the tilt adjusting bolt. When installing the space, the second profile is first mounted/arranged against the uneven surface. In present embodiment, the surface may be tilted with respect to the horizontal. The first bolt and the second bolt are adjusted to make the first profile horizontal.

When a sensor is used, it may optionally be selected from a group of a motion sensor, a $CO_2$ sensor, a light sensor, a temperature sensor and a pressure sensor. The motion sensor is configured to detect the presence of a user inside the enclosed space. The $CO_2$ sensor is configured to detect the carbon-dioxide level inside the enclosed space. The temperature sensor is configured to detect the temperature inside the enclosed space. The pressure sensor is configured to detect the pressure inside and outside the enclosed space. The enclosed space may also comprise any combination of these sensors, such as two, three, four or five of the sensors, freely chosen.

In an embodiment, the controller may turn the visible light on when the user enters the enclosed space. The controller is configured to limit usage of the dedicated wavelengths if there is a person inside the space. The controller may also control the light source to emit light in the dedicated cleaning range when the user leaves the enclosed space to kill the germs. The controller may further control the input air fan to bring fresh air inside the enclosed space, i.e. to "flush" the space with air to refresh the space after the usage.

A typical facility according to the present description comprises a space with a plurality of walls, a sliding door, a controller, a sensor and a light source. At least one of the walls includes an opening (closable with the sliding door) for accessing the enclosed space. The door includes two parallel glass panels slidable on opposite sides of the front wall of the space. The sliding door encloses a low friction part with springs and moves in vertical direction when a user slides the door. The height and inclination of the base structure with the help of tilt adjustment bolts.

An input air fan is coupled to the ceiling of the space and includes an air filter. The ceiling of the space further includes an air outlet with a flow meter configured to provide flow information to the controller. The sensor provides presence information of the user to the controller. The light source emits light alternately in the visible range and in the dedicated cleaning range depending upon the presence of the user inside the space.

In an embodiment the dedicated cleaning range can be blue light (450-495 nm). It is also possible to use more than one dedicated cleaning range, in which case a second range could be for example ultra violet light (380-450 nm).

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

DETAILED DESCRIPTION OF THE DRAWINGS

Figure 1:
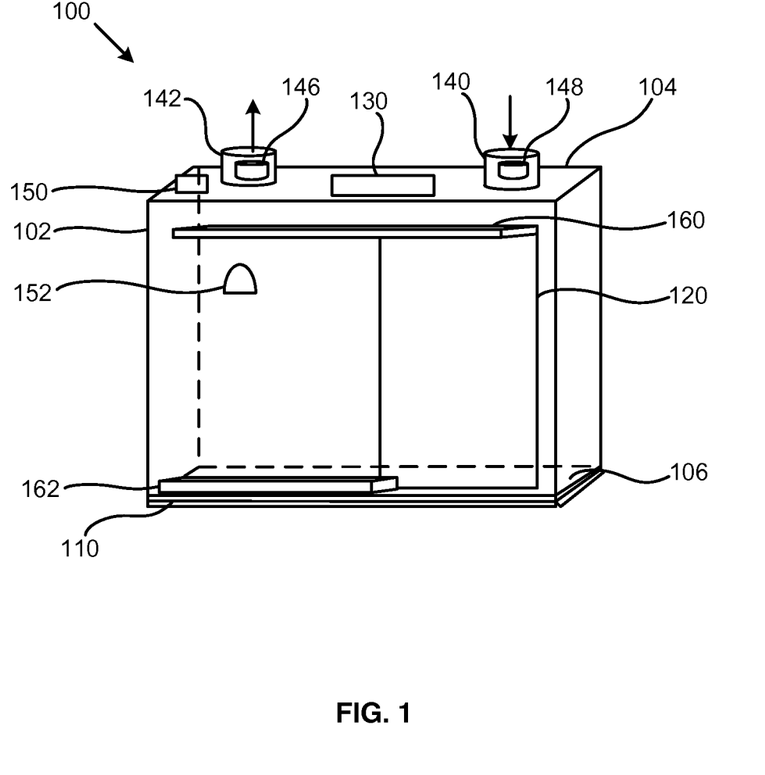
FIG. 1 illustrates an overview of a space according to an embodiment herein.

FIG. 1 illustrates an overview of a space 100. The space 100 includes four walls including a front wall 102, a floor 106, a ceiling 104, an input air fan 140, an output air pipe 142, and a controller 150. The input air fan 140 and the output air pipe 142 are mounted on the ceiling 104. The input air fan 140 has a filter 148 and the output air pipe 142 has an air flow meter 146. A light source 130 is attached to the ceiling 104.

The space 100 further includes a sensor 152. The space 100 further includes a door 120 and a base structure 110. The door 120 is a sliding door which is configured to run between an upper track 160 and a lower track 162. The base structure 110 is adjustable for adjusting a tilting angle of the base in relation to walls of the space 100 and ground on which the space 100 is placed.

Figure 2:
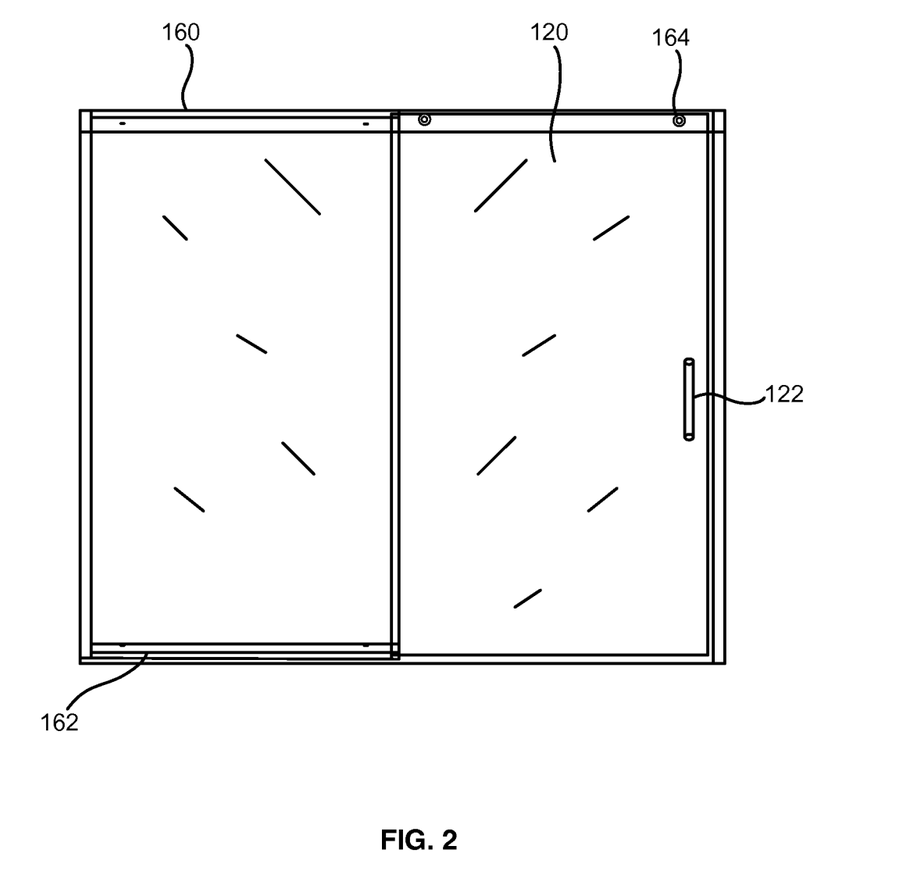
FIG. 2 illustrates a detailed structure of the door according to an embodiment herein.

FIG. 2 illustrates a detailed structure of the door 120. The upper track 160 incorporates a first groove for 164 to hang the door 120 from the upper track 160. The lower track 162 incorporates a second groove to keep the door 120 stable when the user moves the door 120 with the help of a handle 122.

Figure 3:
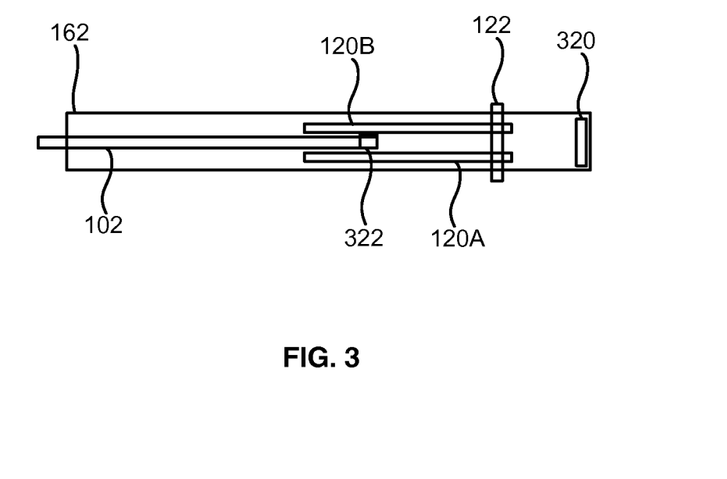
FIG. 3 shows the top view of the door according to an embodiment herein.

FIG. 3 shows the top view of the door 120. The door 120 includes a first door part 120A and a second door part 120B. The parts are mounted together with the handle 122 and also kept together with the lower track 162 (and the upper track, not shown in the FIG. 3). A stopper part 320 is arranged to stop the sliding of the door 120. A protrusion 322 is arranged in the part of the front wall 102.

Figure 4:
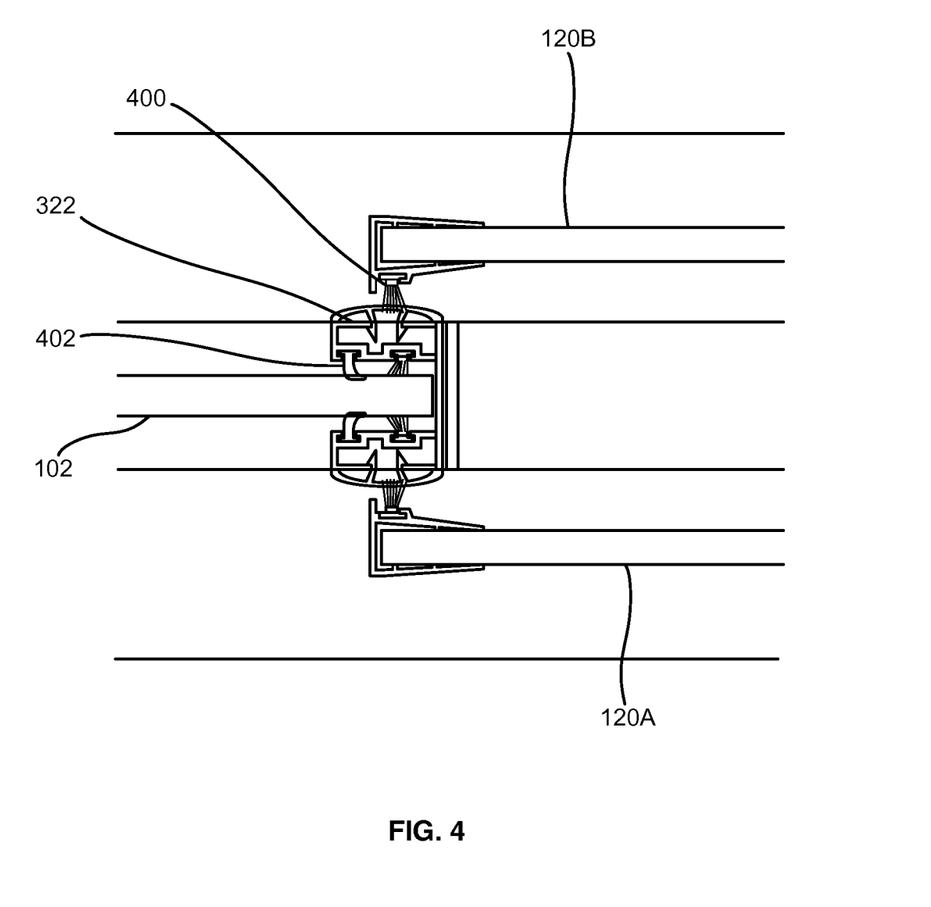
FIG. 4 shows more details of the door arrangement according to an embodiment herein.

FIG. 4 shows more details of the door 120 arrangement according to an embodiment herein. A plurality of brushes 400 isolate the air flow partially. A rubber part 402 provides mechanical support for the protrusion 322.

Figure 5:
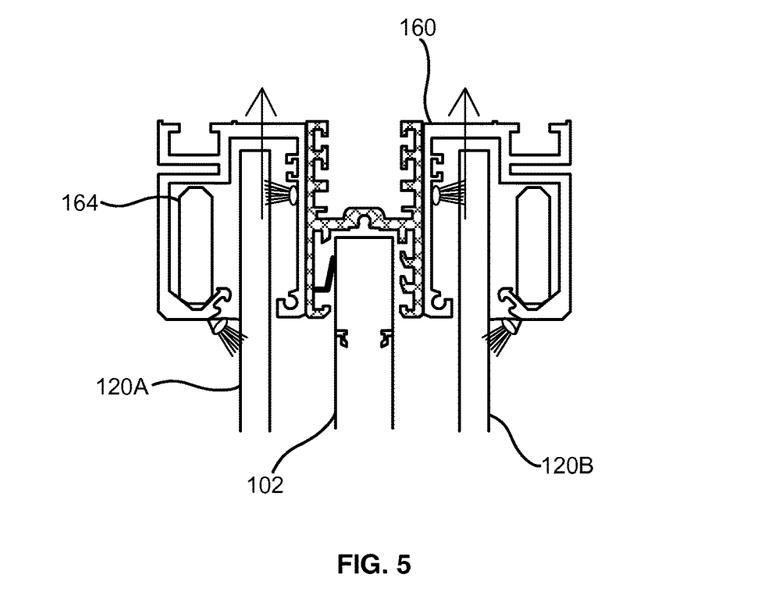
FIG. 5 illustrates the details of the upper track according to an embodiment herein.

FIG. 5 illustrates the details of the upper track 160. The rollers 164 are in the first groove of the upper track 160. The first door part 120A and the second door part 120B include separate set of rollers. The door 120 is arranged to slide on both sides of the front wall 102.

Figure 6:
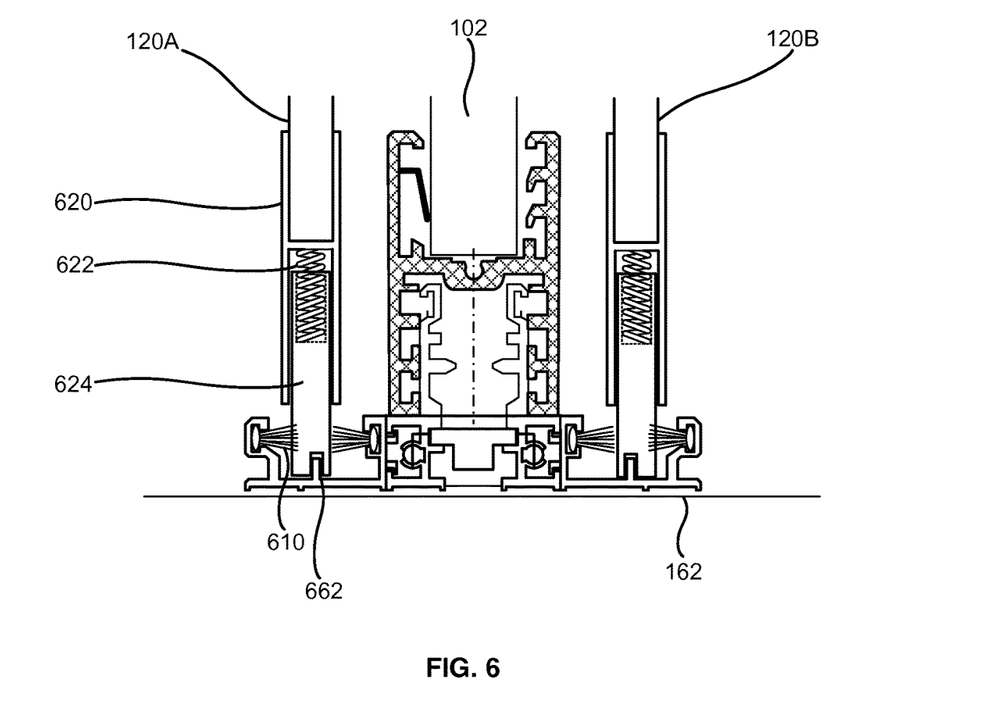
FIG. 6 illustrates the lower track and the arrangement of various parts of the door according to an embodiment herein.

FIG. 6 illustrates the lower track 162 and the arrangement of various parts of the door 120. The first door part 120A and the second door part 120B house an H-profile 620 in the lower side. The H-profile 620 includes a plurality of springs 622. A low friction part 624 is configured to run in the protrusion 662 of the lower track 162. A plurality of brushes 610 is employed to prevent air flow.

Figure 7:
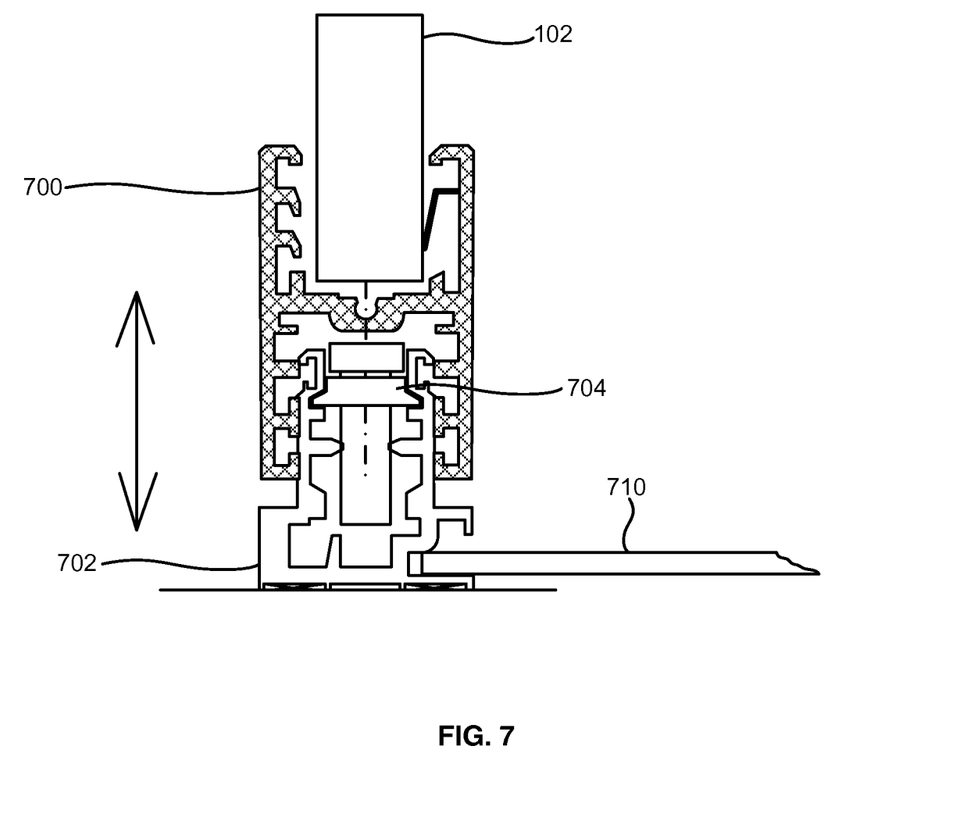
FIG. 7 is an illustration of a plurality of elements of the base structure of the space according to an embodiment herein.

FIG. 7 is an illustration of a plurality of elements of the base structure 110 of the space 100. The base structure 110 includes a first profile 700, a second profile 702, and a floor 710. The wall element 102 is mounted in the first profile 700. The first profile 700 partly covers the second profile 702. The second profile 702 is arranged to be in contact with the ground. The floor 710 of the space 100 may be mounted to the second profile 702. A tilting adjusting bolt 704 is arranged to the second profile 702.

Figure 8:
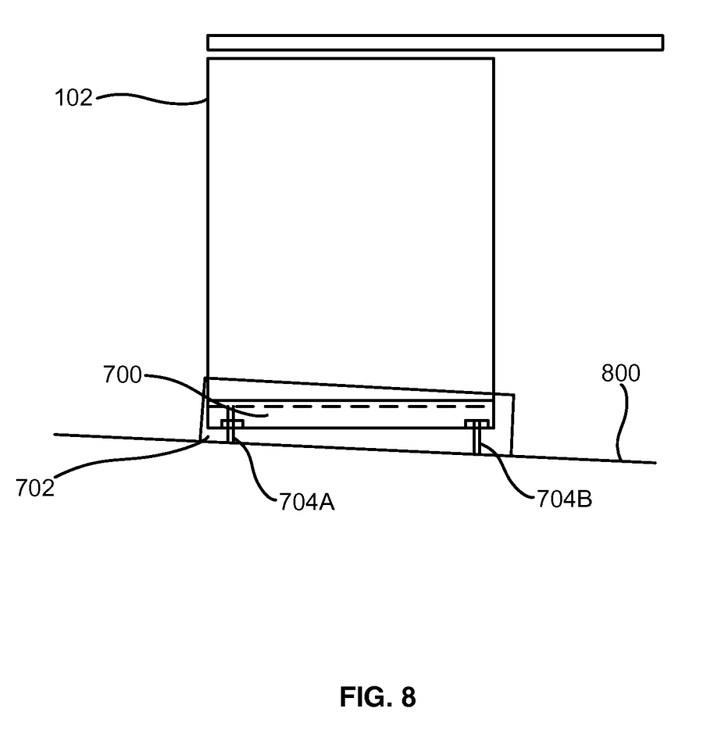
FIG. 8 shows an embodiment showing installation of the wall element in an uneven surface according to an embodiment herein.

FIG. 8 shows an embodiment showing installation of the wall element 102 in an uneven surface 800. The first profile 700 couples to the wall element 102. A first bolt 704A is on the left side and a second bolt 704B on the right side in respect to FIG. 8.

Figure 9A:
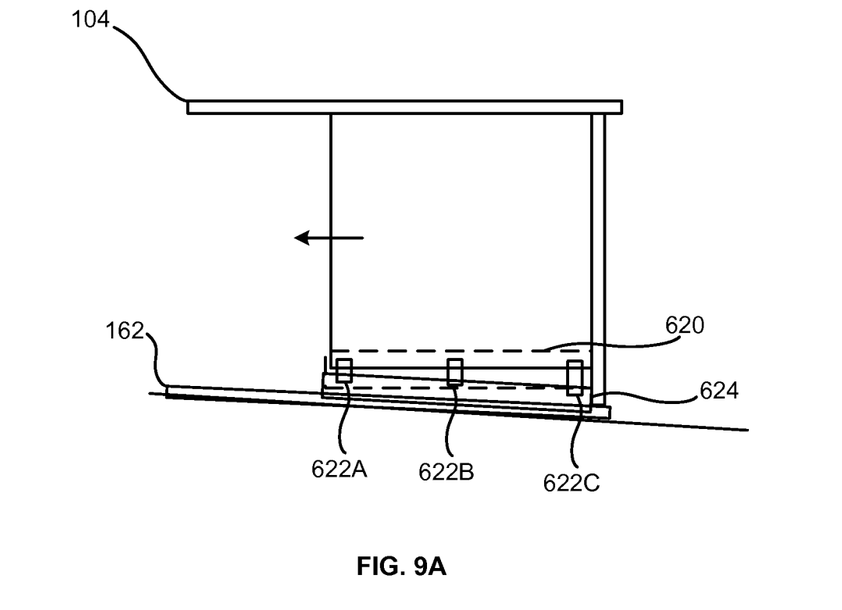
FIG. 9A and FIG. 9B illustrate the sliding door configured to move left to right and right to left on the uneven surface according to an embodiment herein.
Figure 9B:
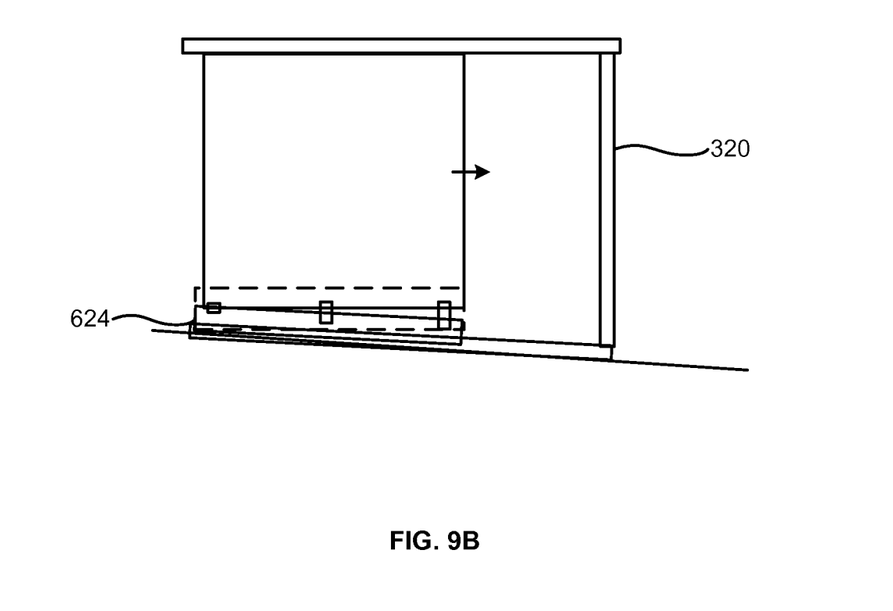

FIG. 9A and FIG. 9B illustrate the sliding door 120 configured to move left to right and right to left on the uneven surface. The H-profile 620 is indicated with dotted line for clarity purposes. In FIG. 9A, when the door 120 is closed, where the door 120 is in contact with the stopper 320, the plurality of springs 622A, 622B and 622C are less compressed than when the door is open (FIG. 9B).

Figure 10:
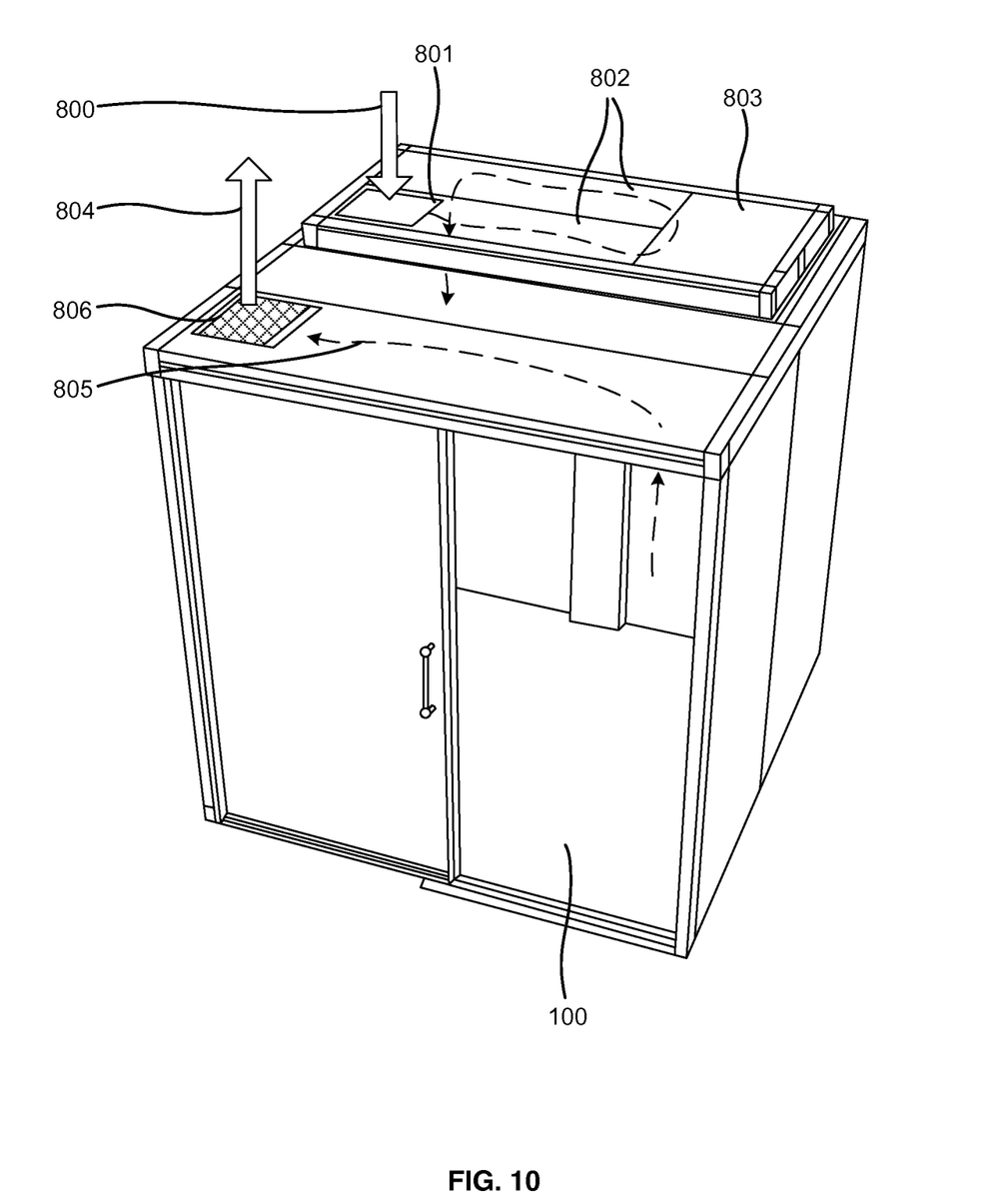
FIG. 10 illustrates an example of ventilation according to an embodiment.

FIG. 10 illustrates an example of ventilation according to an embodiment. In this embodiment, incoming air (illustrated by arrow 800) is directed to an enclosed space 100 via a pre-filter 801, a voice-trap 802 and a HEPA-filter 803. The voice-trap 802 is arranged in two parts, on either side of the HEPA-filter 803. The first part of the voice-trap 802 is also equipped with an electrical fan. The fan may be suitable for moving 30-300 litres of air/s.

The outgoing air (shown with the arrow 804) is arranged to pass though a pre-filter (not illustrated), a voice-trap 805 and a ventilation grate 806 back into the surrounding air.

The invention claimed is:

1. An enclosed space comprising:
   a ceiling;
   a base structure, wherein a height and an inclination of said base structure are arranged to be adjustable, wherein said base structure comprises
   a first profile;
   a second profile, wherein said second profile is arrangeable to be in contact with a ground and is an integral part of a floor of said enclosed space; and
   one or more bolts for arranging a tilting angle between said first profile and said second profile;
   a plurality of walls, wherein at least one of the walls comprises an opening to allow access to said enclosed space;
   at least one sliding door arranged to close the opening, wherein said sliding door comprises two parallel glass panels;
   a controller;
   an input air fan equipped with an air filter; and
   an air outlet equipped with a flow meter configured to provide flow information to said controller;
   wherein said controller is configured to control said input air fan based on the flow information from said flow meter.

2. The enclosed space according to claim 1, wherein the at least one sliding door comprises a handle.

3. The enclosed space according to claim 2, wherein the at least one sliding door is configured to run between an upper track and a lower track with one or more rollers.

4. The enclosed space according to claim 3, wherein said lower track includes an H-profile.

5. The enclosed space according to claim 4, wherein said H-profile comprises a plurality of springs.

6. The enclosed space according to claim 3, wherein the glass panels are arranged to slide in opposite sides of the at least one of the walls of said enclosed space.

7. The enclosed space according to claim 3, wherein the at least one sliding door further comprises a low friction part that is arranged to engage a surface part of the lower track.

8. The enclosed space according to claim 7, wherein said low friction part is arranged to run in a protrusion of said lower track.

9. The enclosed space according to claim 3, wherein said at least one sliding door comprises:
   a stopper to stop the at least one sliding door;

a protrusion, wherein said protrusion forms part of a seal arrangement to prevent air leakage from said enclosed space;

a rubber part to support said protrusion; and a plurality of brushes, arranged to prevent air flow.

10. The enclosed space according to claim 1, further comprising a sensor configured to provide presence information to said controller, and said controller is configured to control a light source based on the presence information from said sensor.

11. The enclosed space according to claim 10, wherein said sensor is selected from a group comprising a motion sensor configured to detect a presence of a user inside said enclosed space;

a $CO_2$ sensor configured to detect a carbon-dioxide level inside said enclosed space;

a light sensor;

a temperature sensor configured to detect a temperature inside said enclosed space; and a pressure sensor configured to detect a pressure inside and outside said enclosed space.

12. The enclosed space according to claim 1, further comprising a light source configured to emit light alternately in the visible range and in a dedicated cleaning range.

13. The enclosed space according to claim 12, wherein said light source is configured to emit ultraviolet or blue light to kill germs inside said enclosed space.

14. The enclosed space according to claim 12, wherein said controller is configured to control said light source to emit light in the dedicated cleaning range when a user has left said enclosed space and to turn the visible light on when a user is entering said enclosed space.

15. The enclosed space according to claim 12, wherein the dedicated cleaning range is 450-495 nm.

16. The enclosed space according to claim 1, wherein the first profile slidably receives a part of the second profile.

17. The enclosed space according to claim 16, wherein the first profile rests on the second profile when the one or more bolts are not used for arranging the tilting angle between the first profile and the second profile.

* * * * *